United States Patent [19]
Piran et al.

[11] Patent Number: 5,817,527
[45] Date of Patent: Oct. 6, 1998

[54] CONJUGATION OF LIGAND TO IMMOBILIZED PROTEIN IN ORGANIC SOLVENT

[75] Inventors: Uri Piran, Sharon; Steve C. S. Chang, Franklin; William J. Riordan, Mansfield; James W. Peterson, Attleboro; Edward M. Sunshine, Plainville, all of Mass.

[73] Assignee: Chiron Diagnostics Corporation, East Walpole, Mass.

[21] Appl. No.: 554,013

[22] Filed: Nov. 6, 1995

[51] Int. Cl.$^6$ ............... G01N 33/546; G01N 33/552; G01N 33/553
[52] U.S. Cl. ............... 436/527; 436/526; 436/529; 436/530; 436/533; 530/807; 530/811; 530/814; 530/815
[58] Field of Search ............... 436/526, 527, 436/529, 530, 533; 530/814, 815, 811, 807

[56] References Cited

U.S. PATENT DOCUMENTS

| | | | |
|---|---|---|---|
| 4,670,383 | 6/1987 | Baier et al. | 435/7 |
| 4,788,136 | 11/1988 | Grenier et al. | 436/539 |
| 4,824,777 | 4/1989 | Chang et al. | 435/7 |
| 5,196,349 | 3/1993 | Piran et al. | 436/500 |
| 5,445,936 | 8/1995 | Piran et al. | 4435/6 |
| 5,482,996 | 1/1996 | Russell et al. | 525/54.1 |

FOREIGN PATENT DOCUMENTS

| | | | |
|---|---|---|---|
| WO 9010709 | 9/1990 | WIPO | C12P 21/08 |

OTHER PUBLICATIONS

P. Cuatrecasas, J. Biol. Chem., vol. 245, No. 12, Issue of Jun. 25, pp. 3059–3065 Jun. 1970.

P. Cuatrecasas et al., Methods in Enzymology, vol. 22, pp. 345–378.

Dudley, R.F. (1991) J. Clin Imunoassay; 14:77–82.

Wong S.S. Chemistry of Protein Conjugation and Cross–Linking, CRC Press Inc. (1991), pp. 7–48.

Scouten, Ed. (1983) Solid Phase Biochemistry, John Wiley & Sons, pp. 99–100.

Wood, W.G. and Gadow, A. (1983) J. Clin Chem Clin Biochem; 21:789–797.

Gadow, A. et al (1984) J. Clin Chem Clin Biochem; 22:337–347.

Wood, W.G. et al (1984) J. Clin Chem Clin Biochem; 22:349–356.

Freytag, J.W. et al (1984) Clin Chem; 30:417–420.

Wilchek, M. and Miron T. (1974) Methods in Enzymology; 34:72–77.

Piran et al (1993) Clin Chem; 39:879–883 (1993).

Piran et al (1990) J Immunol Methods; 133:207–214.

*Primary Examiner*—Mary E. Ceperley
*Attorney, Agent, or Firm*—Arthur S. Morgenstern; Robert P. Blackburn

[57] ABSTRACT

A new method for immobilization of small molecules on solid supports via a macromolecular spacer has been developed. A protein or another macromolecule is first immobilized in an aqueous medium, and the solid support is than washed with an organic solvent. The small molecule is coupled in an organic medium, followed by organic medium washes. The new solid phases are useful for affinity purifications, immunoassays and other binding assays, and for selection of binders by panning procedures.

12 Claims, 6 Drawing Sheets

CONJUGATION OF LIGAND TO IMMOBILIZED PROTEIN IN ORGANIC SOLVENT

BACKGROUND

The subject of the present invention involves a method for preparation of affinity supports for affinity separations. The principles of affinity separation, also termed affinity chromatography, bioselective adsorption, and biomolecular recognition methods, are described in detail in several books and review articles, such as: Handbook of Affinity Chromatography (1993) T. Kline, Ed., Marcel Dekker, Inc.; Affinity Chromatography: a Practical Approach (1985) Dean P. D. G., Johnson W. S., and Middle F. A. Eds., IRL Press; Solid Phase Biochemistry (1981) Scouten W. H. Eds., John Wiley & Sons; Current Trends in Molecular Recognition and Bioseparation (1995) Jones C. et al. Journal of Chromatography A, 707:3–22. Affinity separations are specific and efficient methods, but often they do not perform as well as theoretically expected, due to a number of technical problems, as described in the references cited above. Some of the main problems are 1. ligand leaking (or leaching), i.e. the specific molecule attached to the solid support (ligand) slowly but constantly separates from the support, leading to reduction of separation efficiency and to contaminations. 2. Non-specific binding of undesirable molecules to the support by a mechanism that is different from the specific binding to the ligand. These molecules often co-elute with the desired molecule, thus reducing the efficiency of separation.

Although the most often discussed application of affinity separation is affinity chromatography for purification of proteins and messenger RNA, we discuss herein other important applications. One application is the use of solid supports for immunoassays and the other is for the process of "panning", namely, affinity selection of specific clones of phage or other microorganisms displaying specific binders on their surface, or selection from combinatorial libraries of peptides or oligonucleotides.

In solid phase (heterogeneous) immunoassay technology, the analyte can be the binding partner that carries the label (signal-generating species, such as radioisotopes, enzymes, fluorescent compounds, or chemiluminescent compounds), while the antibody is immobilized on the solid phase. For discussion of immunoassays see Chard T. ( Ed.) "An Introduction to Radioimmunoassay and Related Techniques" (1983) North Holland, New York.; Maggio E. T. (Ed.) "Enzyme Immunoassay "(1980) CRC Press, Boca Raton, Florida; Gerson B. Fluorescence Immunoassay. J. Clin. Immunoassay 7(1):73–81,1984; Seitz W. R. Immunoassay Labels Based on Chemiluminescence and Bioluminescence. Clin Biochem (Canada) 17(2): 120–125, 1984. Alternatively, the antibody can be the labeled species, while an analyte derivative is immobilized to a solid phase, as described by Miles, L.E.M et al. (1968) Nature, 219:186–180 and others. Since the production of mouse monoclonal antibodies became practical in 1975, assay architectures with labeled antibodies became more attractive because of the greater ease with which monoclonals can be obtained reproducibly and in large quantities. In addition, purifying and labeling monoclonal antibodies is relatively easy, since it does not require affinity purification, a step that is essential for labeling polyclonal antibodies. Also, it is often difficult to conjugate small molecular mass analytes (molecule with formula weight under about 1000 daltons) to signal-generating molecules and to purify the desired product afterwards. In addition, competitive immunoassay formats utilizing solid phase-immobilized analyte and liquid phase labeled antibody give higher sensitivity due to the higher affinity of liquid phase antibody.

Coupling of antibodies and other specific binders, which are biological macromolecules, to the solid phase is relatively easy, since both the solid phase and the macromolecules are soluble in aqueous medium. The coupling can be adsorptive or by covalent bonds via the use of cross-linking agents such as glutaraldehyde. The reaction can be done in one or more steps; however, bringing the solid phase in contact with the macromolecule is carried out in a water solution, and the uncoupled fraction of the macromolecules can be easily washed out with aqueous media in order to avoid the presence of residual uncoupled specific binder in the assay reagent. If the uncoupled protein is not removed, it will leak and lead to a functionally unstable solid phase. Antibodies, other proteins, macromolecules and polymers are attached to the solid support via several attachment points, which ensures a very stable immobilization, and consequently low leaking.

In contrast, current methods of coupling small molecular mass molecules, such as haptens, to solid phases (immobilizations) are more problematic because most small molecular mass analytes of biological interest require a spacer group between them and the support in order to make them accessible for binding by the ligate (binder in solution). This is particularly true of haptens and other small molecular mass molecules which are relatively hydrophobic and, thus, insoluble or slightly soluble in water. Small ligands are also more susceptible to leaking because they are attached to the support by a single bond.

Current methods for coupling small molecular mass haptens involve three basic approaches. In the first approach, the small molecule is first dissolved in a small volume of organic solvent, which is then added to an aqueous solution of a protein or another water soluble macromolecule in a large volume of aqueous medium. Thus, the conjugation reaction is carried out in the presence of a large amount of water. After the coupling, the purification of the macromolecule-small molecule conjugate and its coupling to the solid support are carried out in a predominantly aqueous medium. (Wood, W. G., and Gadow, A. (1983) J. Clin Chem Clin Biochem 21:789–797; Gadow, A. et al. (1984) J Clin Chem Clin Biochem 22:337–347; Wood, W. G. et al. (1984) J Clin Chem Clin Biochem 22:349–356); Freytag J. W. et al. (1984) Clin Chem 30:417–420; Grenier F. C. et al. (1988) U.S. Pat. No. 4,788,136; Baier, M. et al. (1987) U.S. Pat. No. 4,670,383). This approach usually generates a precipitate consisting of the macromolecule, heavily substituted conjugates and the small molecule itself. In our previous studies using the first approach, we used up to iodothyronine/protein molar ratio of 18, which produced conjugates with a molar ratio of 1.5 (Piran U et al. (1993) J Immunol Methods 133:207–214). When we increased the input ratio to 30 or 50 in order to increase the output ratio, the resulting conjugates became insoluble and could not be used for immunoassays. Thus, the first approach cannot be used when there is a high ratio of hapten to macromolecule. The method is also lengthy and requires extensive conjugate purification. Furthermore, some of the precipitated small ligand cannot be removed from the desired conjugate, and this leads to a high level of small molecule leakage into the assay reagent. This causes a decrease of binding, as was shown by Piran U and Stastny M, U.S. Pat. No. 5,196,349 (1993), thus compromising assay performance. The second approach involves direct reaction of the small molecule with the solid phase in either aqueous or organic media or a combination thereof. This approach is simpler, but it leads to leaking of the small ligand because only a single bond attaches the ligand to the solid phase. The third approach involves first attaching a hydrophilic macromolecule to the support and then reacting the solid support-macromolecule complex with the small ligand in a predominantly aqueous medium and a small amount of organic solvent (necessary to keep the hapten at least partially in solution), as described by Wilchek, M. and Miron T. (1974) in Methods in Enzymology, Jakoby, W. B. and Wilchek, M. Eds., 34:72–77; and Chang, S. C. S. et al (1989) U.S. Pat. No. 4,824,777. Unfortunately, this leads to entrapment of precipitated hydrophobic haptens on the solid phase and to noncovalent adsorption of the small ligand to the solid phase, which, in turn leads to extensive leakage of the ligand. These practices have additional drawbacks: coupling efficiency is low because most of the activated small ligands are nucleophiles and are easily hydrolyzed in aqueous media even at low pH. Also, poor solubility of many small ligands in aqueous medium demands an extensive dialysis step and other water-based purification methods to remove the uncoupled ligand from the solid phase. This is not only time-consuming, but also generates a large quantity of potentially bio-hazardous waste. The use of immobilized small ligands is not restricted to immunoassays: preparation of recombinant antibody fragments and other binding proteins by phage display and other recombinant DNA techniques often requires immobilized haptens for "panning" and screening by such methods as ELISA. The immobilization for these applications is currently achieved by essentially the methods described above. The present invention describes a new approach that avoids the aforementioned problems.

SUMMARY OF THE INVENTION

A new method for immobilization of small molecules on solid supports via a macromolecular spacer has been developed. A protein or another macromolecule is first immobilized in an aqueous medium, and the solid support is then washed with an organic solvent. The small molecule is coupled in an organic medium, followed by organic medium washes. The new solid phases are useful for affinity purifications, immunoassays and other binding assays, and for selection of binders by panning procedures.

DETAILED DESCRIPTION OF THE INVENTION

An improved method for immobilization of small, relatively hydrophobic ligands to solid phases is described herein. This method is useful for use as an affinity separation support in immunoassays for hapten analytes, affinity chromatography for purification of macromolecules, screening of specific binders produced by hybridoma or recombinant DNA techniques, and "panning" procedures in phage display and other protein engineering techniques. The method is faster, more convenient, generates less biohazardous waste, allows use of higher ligand concentrations during the conjugation, and leads to improved performance and stability of the solid phase-small molecule preparations.

The solid phase is first coupled to a protein, a polyaminoacid or another water soluble macromolecule. Alternatively, the solid support can be obtained already precoated with a protein, thus eliminating the need for the first step. This generates a spacer that is firmly attached to the solid support via multiple bonds. Immobilization of proteins or other macromolecules can be done in an aqueous medium either by adsorption, but preferably by covalent bonding by reagents such as glutaraldehyde, carbodiimide and many others. The aqueous medium is then removed, and the solid phase is washed by an organic solvent to remove traces of water, thus increasing the solubility of the hydrophobic small molecule. In addition the removal of water reduces interference with the chemistry of coupling of the small molecule to the solid phase-macromolecule complex when the reaction is sensitive to water. The preferred organic solvent is an aliphatic alcohol (with or without small amounts of other organic solvents or water). The small ligand is dissolved in the aliphatic alcohol, mixed and reacted with the solid phase in an aliphatic alcohol. In such organic environment the coupling is more efficient and predictable because the hydrophobic small ligand is in true solution even at high concentrations; in addition, hydrolysis of the activated ligand or activated solid support is in many cases avoided.

Proteins and other macromolecules undergo denaturation, unfolding and precipitation in most organic solvents, including alcohols. Solid phase-immobilized macromolecules also undergo denaturation: applicant found that immobilized antibodies completely lose their antigen binding activity even by exposure to methanol or ethanol for a few minutes at 25C. However, applicants unexpectedly found that these alcohols do not cause deterioration of the functionality of the solid phase or the spacer macromolecule. Surprisingly, the method allowed the use of very high ligand/protein molar ratios without causing formation of precipitates of conjugate or ligand. For example, in the new method (see Example 1) we used iodothyronine/BGG molar ratio of about 200 without forming precipitates, whereas the use of a molar ratio of 200 when reacting BGG and iodothyronines in aqueous solutions gives massive precipitation. After the coupling of the small ligand to the solid phase or to a protein that is immobilized on the solid phase, an organic solvent, such as alcohol, is used to extensively wash away any uncoupled small ligand. This wash step is more efficient than a wash with an aqueous medium because an aqueous solution is not efficient at solubilizing and removing residual ligand. Since the unreacted small ligand is highly soluble in alcohols, it is efficiently removed by the organic washes, and by the time the solid phase is immersed or additionally washed with an aqueous medium, virtually no unreacted small ligand is present in the solid phase preparation. The preferred organic solvent for both the coupling reaction and the washes is an alcohol, such as methanol, ethanol or propanol, although higher molecular mass aliphatic alcohols may be used. Furthermore, many solid phase-macromolecule spacer complexes are compatible with dioxane, DMF and organic solvents of higher hydrophobicity, such as hydrocarbons. The organic medium can also contain a small amount of other organic solvents, but preferably less than about 10% (v/v). For many applications, 95% ethanol, which contains 5% water may be used. 95% ethanol is a readily available, inexpensive and relatively non-toxic solvent. However, the medium should be predominantly organic, with up to about 10% v/v water. After the washing, the organic solvent is removed by applying a centrifugal, magnetic, or gravitational forces to the solid phase, or, in the case of an extended surface, by decantation, and the solid phase is immersed in an aqueous solution.

The examples shown herein include small ligands that are extremely hydrophobic and are haptens (triiodothyronine, diiodothyronine and pregnenolone). Also shown is an example involving the moderately hydrophobic hapten estradiol. We also successfully used the method for several other steroids, as well as for immobilizing the slightly hydrophobic haptens melatonin, scrotonin and their analogs. Thus, the present invention can be applied to haptens of varying degrees of hydrophobicity or water solubility. We immobilized ligands that are hapten-heterologous, namely analogs that in the unimmobilized form bind the antibody weakly but in the immobilized form bind with greater avidity. For discussion of heterology and its beneficial effects in immunoassays see Piran et al. Clin Chem 39:879–883 (1993) and Piran et al. J Immunol Methods 133:207–214 (1990). However, the method of the present invention is also effective in immobilizing non-heterologous ligands.

The haptens included in the examples, triiodothyronine (T3), estradiol, pregnenolone, and diiodotyronine (T2), were all pre-activated through the endogenous or grafted carboxyl group of the hapten by conjugating it to N-hydroxyl succinimide via dicycl ohexylcarbodiimide (DCC) to form a N-hydroxyl succinimidyl (NHS) compound with a generic chemical form shown below:

After proper purification this NHS-hapten can be stored in dry form in a freezer with good stability until used. In some experiments the coupling was successful even though the unreacted DCC and by-products of the activation reaction were not removed. Many other methods of activation of the hapten can be used.

Alternatively, the solid phase can be activated instead. The chemistry used for immobilization may involve an active ester, maleimide, sulthydryl or one of many other chemistries known in the art. Many such chemistries are described in Dean PDG et al. Eds. "Affinity Chromatography, a Practical Approach" IRL, Press, Oxford/Washington DC (1985) and in Wong SS "Chemistry of Protein Conjugation and Cross Linking" CRC Press Inc. (1991).

The solid phases in some examples are paramagnetic particles made of iron oxide coated with polymerized amino-silane. Also included are examples using controlled pore glass particles. The method described herein is suitable to these and any other solid support such as polystyrene particles, magnetizable latex particles, microtitre plates, test tubes, petri dishes, agarose, cellulose, dextran, silica, silica gel, nylon, chitin, polyacrylamide, nitrocellulose and many other types of solid phases from natural or synthetic origin. The solid phase can be particulate, extended surface or porous. The preferred solid phases for immunoassays are paramagnetic particles, magnetizable latex particles, controlled pore glass and latex particles; the preferred solid phases for affinity chromatography are agarose and controlled pore glass; the preferred solid phases for panning are petri dishes and magnetizable latex particles.

Proteins and other polymers of biosynthetic or synthetic origins can be used as a macromolecular coating of the solid phase and serve as spacers to which small ligands are then attached in an organic medium. The macromolecule can be bovine gamma globulin (BGG), rabbit gamma globulin, bovine serum albumin (BSA), ovalbumin, gelatin, thyroglobulin, polylysine or any other polymer with a molecular mass of more than about 5000 daltons. They can be used alone or in mixtures. The most preferred macromolecule is BGG. In some experiments the solid phase was not coupled to a protein prior to immobilization of the hapten; this led to a functional solid phase, but its stability was lower than in the case of protein-coated solid phases. Therefore, the preferred embodiment includes a step of covalent or adsorptive immobilization of protein or another macromolecule followed by hapten conjugation. The most preferred embodiment involves covalent immobilization using glutaraldehyde as a cross-linker.

In our experiments the NHS-hapten was typically dissolved in dimethylformamide (DMF), then diluted in anhydrous methanol to a designated concentration and a trace amount of triethylamine was added. Protein-coated solid phases were prewashed with anhydrous methanol before they were reacted with the NHS-activated hapten. The reaction usually took place at room temperature for time periods of between one and 20 hours; however, in two examples the reaction was found to be completed in 20 minutes. Thus the reaction time is expected to range from less than about 1 hour up to greater than about 20 hours, depending upon the particular ligand, spacer, organic phase and the chemistry of activation. After the coupling reaction, the solid phase was washed extensively with methanol to remove the uncoupled but non-covalently bound haptens. The final washed solid phases were resuspended in buffers suitable for immunoassays. Coupling efficiency could be easily found by determining the hapten concentration in the supernatant before and after reaction with the solid phases. This direct estimate of coupling efficiency is basically not feasible in prior art methods because of the precipitates that they cause. Hapten solid phases made by this new method compare favorably with hapten solid phases made by the conventional methods in terms of assay performance and in addition have improved functional stability. They are also prepared with greater ease and speed.

When immobilizing hydrophobic small molecules the preferable method utilizes organic solvent in both the immobilization and the wash steps. However, when immobilizing a moderately hydropohobic small molecules it is possible to use a predominantly organic medium in only the immobilization step or the wash step following immobilization. For example, we immobilized digoxin on PMP-BGG by oxidizing digoxin with sodium periodate in ethanol/water mixture (1:1 v/v) and carried out the conjugation of the activated digoxin to the PMP-BGG in a predominantly aqueous medium, and after the conjugation reaction we washed the PMP-BGG-digoxin three times with pure methanol. This solid phase was found to be effective and stable in a competitive chemiluminometric immunoassay of digitoxin using DMAE-anti-digitoxin monoclonal antibody in the ACS: 180 instrument.

Further variations of this novel development will be apparent to those with skill in the art.

EXAMPLES

The following examples illustrate various aspects of the invention but are not intended to limit its usefulness.

Example 1. Immobilization of diiodothyronine on controlled pore glass

Bovine gamma globulin (BGG) was immobilized on controlled pore glass (CPG) containing surface amino-silane as described by Piran U. et al. (1995) U.S. Pat. No. 5,445,936. CPG-BGG, 100 mg, containing about 10 mg of immobilized BGGwas centrifuged at 2000 rpm for 10 min to sediment the particles. The supernatant aqueous medium was decanted and the sediment was resuspended in 10 ml anhydrous methanol and rocked gently for 10 min. The particles were centrifuged and washed three times with 10 ml methanol by 10 min rocking followed by centrifugation steps, and finally resuspeded in 4 ml anhydrous methanol and 0.01 ml triethylamine in a glass test tube. L-3, 5-diiodothyronine (T2) was coupled to the CPG-BGG by adding to the suspension 10 mg of NHS-activated N-hemisuccinate methyl ester of T2 (in 0.7 ml DMF; this represents a molar ratio of T2/BGG of about 200) followed by 20 hours incubation at about 25 C with gentle rocking. After the coupling the particles were centrifuged and washed three times with 10 ml methanol, followed by two washes with 10 mM sodium phosphate buffer pH 7.4. The particles were then washed twice with PBS/BSA (50 mM sodium phosphate, 100 mM sodium chloride, 1 mM EDTA, 0.2 g/L sodium azide and 1 g/L bovine serum albumin, pH 7.4) and diluted in this buffer to concentration of 10 mg CPG-BGG-T2 per ml.

T2 was also immobilized directly onto the amino-silane groups of the CPG (without BGG spacer) in an identical procedure, as a control reagent designed to verify the advantage of using a macromolecular spacer (See results in Example 3).

Example 2. Affinity purification of anti-T3 using CPG-BGG-T2

A monoclonal anti-T3 was prepared and labeled with an acridinium ester (DMAE) as described by Piran et al. U.S. Pat. No. 5,445,936 (1995). The labeled antibody was affinity purified by incubating it with 1 mg CPG-BGG-T2 from example 1 for 1 hour and then filtering the suspension with an disposable syringe filter with cellulose acetate pore size of 0.2 micron (Corning Glass Works, Corning N.Y.). The particles were washed with PBS/BSA by passing 10 ml of buffer through the filter, and the specifically bound antibody was then eluted by 0.1 M glycine buffer at pH 2.5 and was immediately neutralized by 0.1 M sodium phosphate buffer at pH 8.

Figure 1:
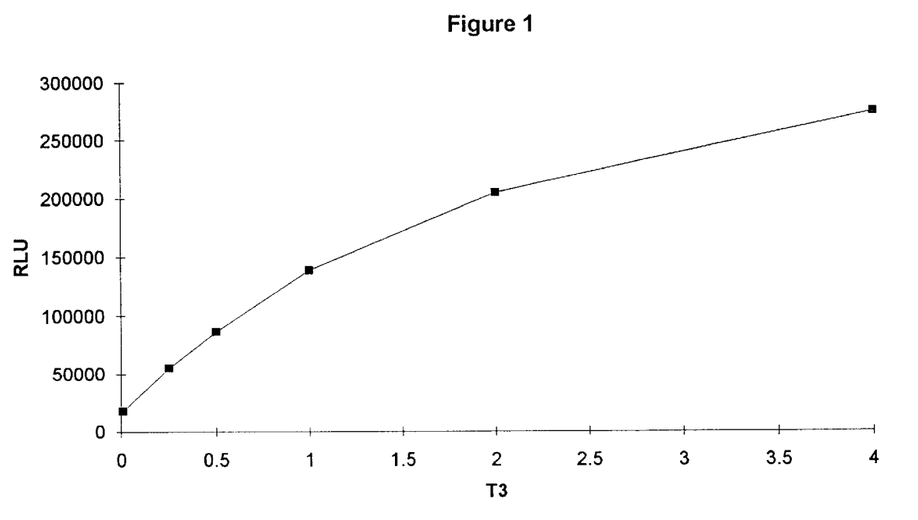
FIG. 1. shows a calibration curve of a non-competitive immunoassay of triiodothyronine (T3) utilizing CPG-BGG-T2 prepared by the new method. Relative light units (RLU) are plotted vs. T3 in ng/ml.

The affinity purified DMAE-anti-T3 and the CPG-BGG-T2, prepared in Example 1, were used to run a calibration curve of T3 in a non-competitive immunoassay format according to Piran et al. U.S. Pat. No. 5,445,936. The calibration curve is shown in FIG. 1.

Example 3. Stability of CPG-BGG-T2 and CPG-T2 compared.

The solid supports prepared in Example 1 were subjected to an accelerated stability test. Both solid phases were diluted to 1 mg/ml in PBS/BSA buffer and incubated at 4 C and 37 C for 7 days. They were then brought to about 25 C and incubated with the affinity purified DMAE-anti-T3 from Example 2 for 10 min, followed by centrifugation and measurement of the DMAE chemiluminescence remaining in the supernatant. Both solid phases bound 98% of the DMAE-anti-T3 after storage at 4 C; however, after 7 days storage at 37C CPG-T2 bound only 83%, while CPG-BGG-T2 bound 94%. Thus, the results show that the method of the present invention is compatible with stabilization of ligand by a protein spacer.

Example 4. Non-competitive immunoassay for free thyroxin

Monoclonal anti-T4 was prepared and labeled with DMAE as described in Piran U and Stastny M, U.S. Pat. No. 5,196,349 (1993). Anti-DMAE monoclonal was prepared and immobilized on paramagnetic particles (PMP) as described by Piran U et al., U.S. Pat. No. 5,445,936 (1995). T3 was coupled to CPG-BGG by the method of the instant invention in methanol, essentially as described for T2 in example 1, except that the activated hapten was the NHS-activated N-methyl ester of L-T3. The DMAE-labeled anti-T4 was affinity purified using CPG-BGG-T3 as the solid support, essentially as described for the affinity purification of DMAE-anti-T3 in Example 2. An aliquot of the affinity purified antibody was incubated with 1 mg CPG-BGG-T3 in 1 ml PBS/BSA for 10 min at about 25 C. The reaction mixture was centrifuged for 10 min at 2000 rpm to sediment the CPG, and a 0.01 mL aliquote of supernatant was taken for chemiluminescence measurement. More than 99% of the labeled antibody was found to bind to CPG-BGG-T3.

These reagents were used for constructing a calibration curve for free T4 (FT4) using the ACS:180 automated immunoassay analyzer (described by Dudley RF, The Ciba-Corning ACS: 180 Automated Immunoassay System. J. Clin. Immunoassay 14:77–82,1991).

Figure 2:
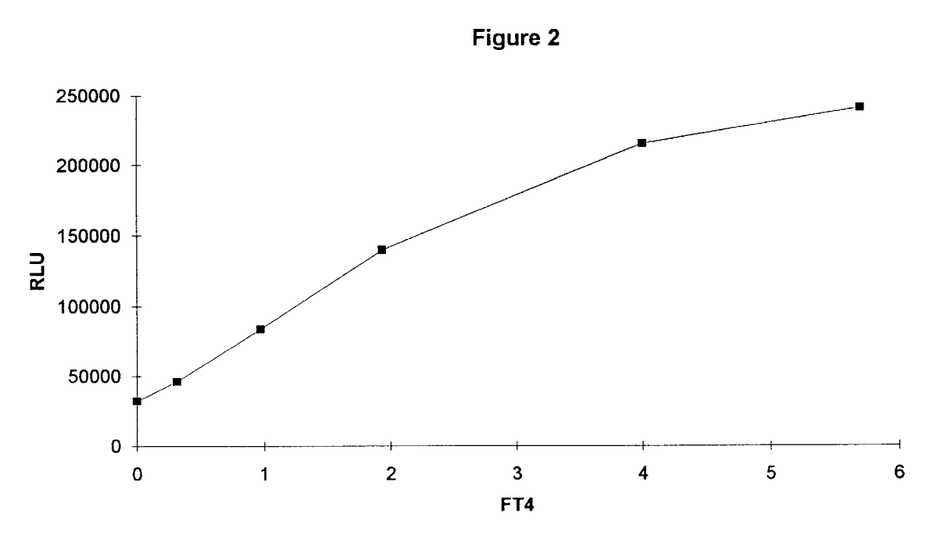
FIG. 2. shows a calibration curve of a non-competitive immunoassay of free thyroxin (FT4) using CPG-BGG-T3 prepared by the new method. Plotted are relative light units (RLU) chemiluminescence vs. free T4 in ng/dL.

The sample probe delivered 0.05 ml human-serum based calibrator, reagent probe 1 delivered 0.1 ml labeled anti-T4 in buffer containing, per liter, 20 mmole sodium barbital, 150 mmole sodium chloride, 1 mmole EDTA, I g BSA and 1.5 g BGG at pH 8.5. After 2.5 min incubation at 37 C reagent probe 2 delivered 0.25 mg CPG-BGG-T3 in 0.1 ml PBS/BSA, and after an additional 2.5 min reagent probe 3 delivered 0.05 mg PMP-anti-DMAE in 0.1 ml PBS/BSA. Magnetic separation, wash steps and chemiluminescent readout were carried out by the instrument as described by Piran U et al. U.S. Pat. No. 5,445,936 (1995). The resulting calibration curve is shown in FIG. 2, demonstrating the utility of the CPG-BGG-T3 prepared by the new method in the assay.

Figure 3:
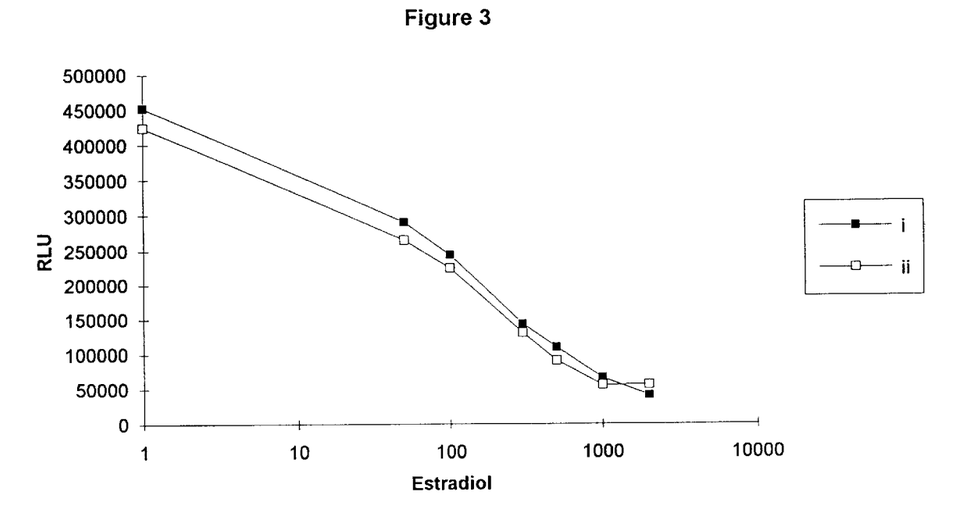
FIG. 3. shows calibration curves of competitive estradiol assays using PMP-BGG-estradiol made by the new method (i) and the conventional method (ii), wherein the conventional method involves first preparing BGG-estradiol and then immobilizing the protein-hormone conjugate on PMP. Relative light units are plotted vs. estradiol concentrations in pg/mL.

Example 5. Preparation of PMP-BGG-estradiol and competitive immunoassay of estradiol PMP-BGG was prepared essentially as described for immobilizing various other proteins by Piran U and Stastny M, U.S. Pat. No. 5,196,349 (1993). Five hundred milligrams of PMP-BGG were washed once with 25 ml of 10 mM sodium phosphate buffer pH 7.4, then five times with 25 ml of anhydrous methanol. The supernatant was removed after each wash by separating magnetizable particles with a magnet. A stock solution of NHS-activated 6-carboxymethyl oxime estradiol in 100% DMF was prepared at concentration of 5.7 mg/ml. The stock solution was diluted 10-fold with methanol containing 23% DMF. Three ml of this solution was diluted further with 27 ml of methanol containing 78 ug/ml of triethylamine. Twenty five ml of this solution was added to the methanol-washed PMP-BGG and the suspension was mixed at 200 rpm/min for 20 minutes at room temperature. At the end of the reaction time the particles were separated on a magnet and the supernatant was removed followed by five methanol washes the same way as described for the 500 g PMP-BGG in this Example. After the fifth methanol wash the PMP-BGG-estradiol solid phase was washed with 10 mM sodium phosphate buffer pH 7.4, and then resuspended in 25 ml of PBS/BSA containing 0.1% sodium azide as preservative. PMP-BGG-estradiol made by this new method was diluted to the same concentration as the reference which was made by the conventional (indirect) method via estradiol-BGG conjugate. The binding characteristic of these two solid phases were generated by the ACS :180 automated immunoassay analyzer and the resulting calibration curve is shown in FIG. 3. Basically, the assay performance of the new solid phase was similar to that of the conventional solid phase and the binding curves of the two solid phases were parallel to each other. However, the new solid phase took only two days to prepare, whereas the reference solid phase took five days. Nearly half of the latter preparation time was used for dialyzing away uncoupled estradiol from the BGG-estradiol conjugate; in contrast, using the present invention this step was efficiently done by a direct organic solvent extraction for about one hour.

Figure 4:
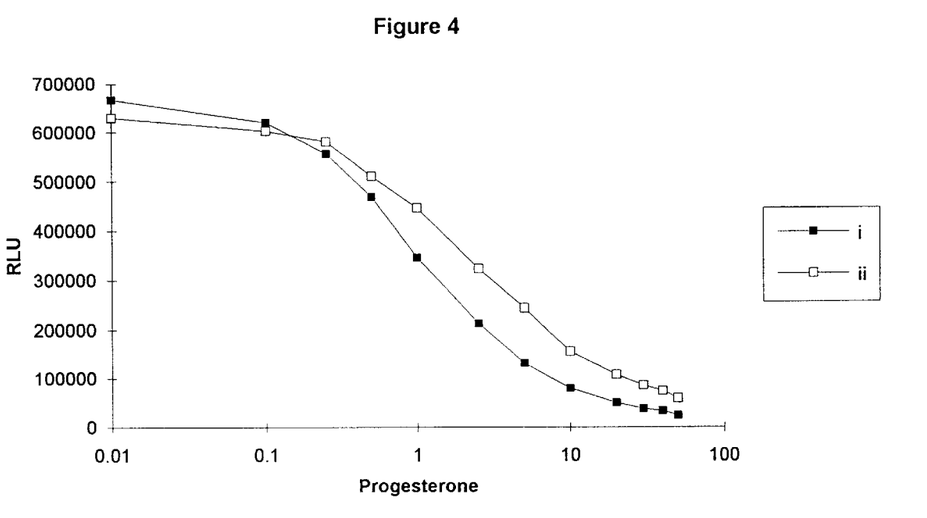
FIG. 4. shows calibration curves of competitive progesterone assay with the new (i) and the conventional (ii) PMP-BGG-pregnenolone as the solid phases, wherein the conventional method involves first preparing BGG-estradiol and then immobilizing the protein-hormone conjugate on PMP. Relative light units are plotted vs. progesterone concentrations in ng/mL.

Example 6. Preparation of PMP-BGG-pregnenolone and competitive immunoassay of progesterone Five hundred milligrams of PMP-BGG were washed once with 25 ml of 10 mM sodium phosphate buffer pH 7.4, then five times with anhydrous methanol as described in Example 5. A stock solution of NHS-pregnenolone in 100% DMF at concentration of 6.3 mg/ml was prepared. Diluted the stock solution 10 folds with methanol containing 23% DMF. Three ml of this solution was diluted further with 27 ml of methanol containing 70 ug/ml of triethylamine. Twenty five ml of the NHS-activated pregnenolone solution last diluted to the methanol-washed BGG-PMP was transferred and mixed at 200 rpm/min for 20 minutes at room temperature. At the end of the reaction time supernatant was removed followed by five methanol washes the same way as before. After the fifth methanol wash the PMP-BGG-pregnenolone solid phase was washed with 10 mM sodium phosphate buffer pH 7.4, then resuspended in 25 ml of PBS buffer contain 0.1% sodium azide as preservative. PMP-BGG-pregnenolone made by this new method was diluted to the same concentration as the reference which was made by the conventional (indirect) method via pregnenolone-BGG conjugate. The binding characteristic of these two solid phases were generated by the ACS:180 analyzer and the result is shown in FIG. 4. Basically, the new solid phase gave a steeper displacement curve than the reference solid phase, thus endowing the assay with better performance characteristics.

Example 7. Preparation of PMP-BGG-T2 and a competitive immunoassay of T3

Five hundred milligrams of BGG-PMP were washed once with 25 ml of 10 mM sodium phosphate buffer pH 7.4, then five times with 25 ml of anhydrous methanol as described in Example 5. Prepared a stock solution of NHS-activated T2 in 100% DMF at concentration of 31.89 mg/ml. Diluted the stock solution 10 folds with methanol containing 23% DMF. Diluted 3 ml of this solution further with 27 ml of methanol containing 70 ug/ml of triethylamine. Transferred 25 ml of the NHS-diiodotyronine solution last diluted to the methanol-washed BGG-PMP and mixed at 200 rpm/min for 20 minutes at room temperature. At the end of the reaction time supernatant was removed followed by five methanol washes the same way as before. After the fifth methanol wash the estradiol-BGG-PMP solid phase was washed with 10 mM sodium phosphate buffer pH 7.4, then resuspended in 25 ml of PBS buffer contain 0.1% BSA, 0.1% sodium azide as preservative. Diiodothyronine BGG-PMP made by this new method was diluted to the same concentration as the reference which was made by the conventional (indirect) method via diiodothyrone-BGG conjugate.

Figure 5:
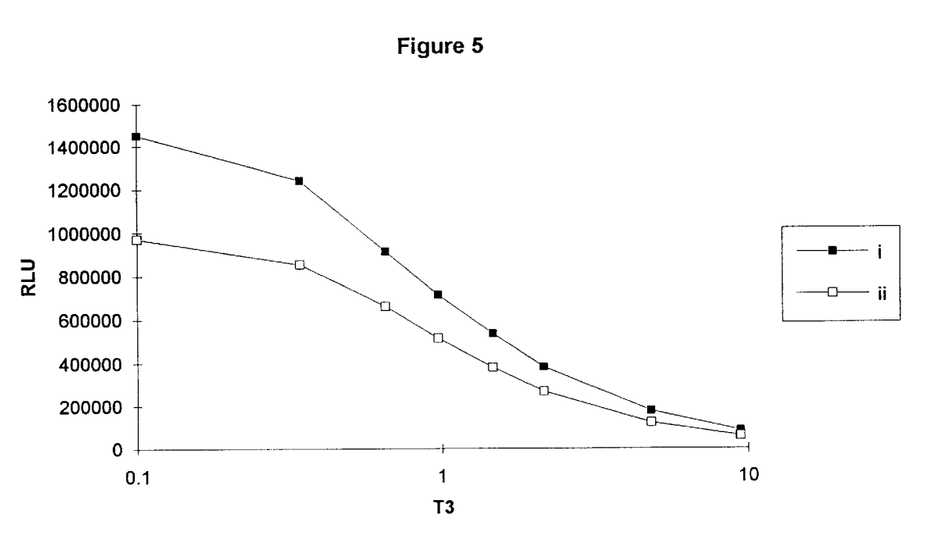
FIG. 5. shows calibration curves of competitive immunoassay of triiodothyronine (T3) using PMP-BGG-T2 made by the new (i) and the conventional (ii) methods, wherein the conventional method involves first preparing BGG-estradiol and then immobilizing the protein-hormone conjugate on PMP. Relative light units are plotted vs. T3 concentrations in ng/mL.
Figure 6:
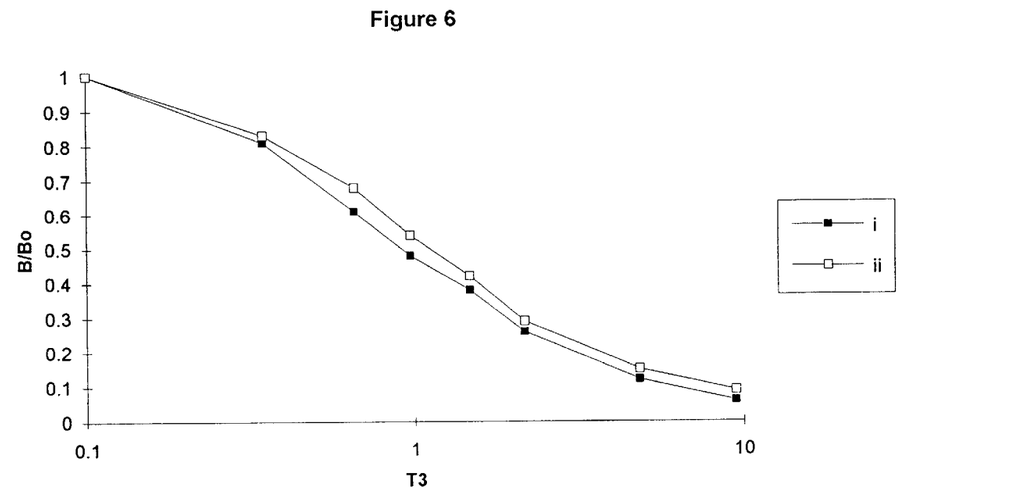
FIG. 6. shows the data of FIG. 5. after normalization to bound signal/bound signal at zero dose (B/B0) vs. T3 concentration.

The binding characteristic of these two solid phases were generated by the ACS:180 analyzer and the results are shown in FIG. 5 . In FIG. 5 it appears that the new solid phase has a higher capacity than the reference solid phase, but this difference could be eliminated by diluting the new solid phase further. Perhaps the most interesting finding is that if the two standard curves are normalized by the a B/Bo versus T3 concentration plot, as shown in FIG. 6, the new solid phase actually gives a steeper displacement curve than the reference one. Again, this is a more desirable situation for competitive assays, especially when the signals are significantly higher.

What is claimed:

1. A method for use in affinity separation, immunoassay and panning, said method comprising coupling a small molecular mass molecule having formula weight under about 1000 daltons to a solid support via the use of a protein spacer, and said method comprising:

a. immobilizing said protein on said solid support to form a solid support-protein complex in a predominantly aqueous medium, followed by washing in a solvent, b. reacting said small molecular mass molecule and said solid support-protein in a solvent, and c. washing said solid support-protein-small molecular mass molecule complex by a solvent, wherein the solvent is predominantly organic in at least step b or step c.

2. A method for coupling a small molecular mass molecule to a solid support via the use of a macromolecule spacer comprising:

a. immobilizing said macromolecule on said solid support to form a solid support-macromolecule complex, b. washing said solid support-macromolecule complex in a solvent that is predominantly organic, c. reacting said small molecular mass molecule and said solid support-macromolecule in a solvent that is predominantly organic to form a solid support-macromolecule-ligand complex, and d. washing said solid support-macromolecule-small molecular mass molecule complex by a solvent that is predominantly organic.

3. The method of claim 1 wherein said solid support is selected from the group consisting of paramagnetic particles, controlled pore glass, agarose, latex particles, polystyrene particles, magnetizable latex particles, microtitre plates, test tubes, petri dishes, agarose, cellulose, dextran, silica, silica gel, nylon, chitin, polyacrylamide, and nitrocellulose.

4. The method of claim 3 wherein said solid support is selected from the group consisting of paramagnetic particles, controlled pore glass, latex particles, magnetizable latex particles, agarose and petri dishes.

5. The method of claim 1 wherein said predominantly organic solvent is:

(a) an aliphatic alcohol, (b) dimethylformamide, or (c) dioxane in the presence of small amounts of other organic solvents or water.

6. The method of claim 1 wherein said small molecular mass molecule coupled to a solid support is used in affinity chromatography, immunoassay or planning.

7. The method of claim 6 wherein said small molecular mass molecule coupled to a solid support is used in affinity chromatography.

8. The method of claim 6 which said immunoassay is for an analyte selected from the group consisting of thyroxin, free thyroxin, triiodothyronine, digitoxin, phenytoin, progesterone and estradiol.

9. The method of claim 1 in which the reaction between said small molecular mass molecule and said solid support-macromolecule takes place for about less than 1 hour to more than about 20 hours.

10. The method of claim 1 wherein said solid support is precoated with a protein.

11. The method of claim 10 in which said protein is BGG.

12. A method for use in affinity separation, immunoassay and panning, said method comprising coupling a small molecular mass molecule having formula weight under about 1000 daltons to a solid support via the use of a biosynthetic macromolecule spacer, said spacer constituting a non-synthetic macromolecule having a unique secondary and tertiary structure, and said method comprising:

a. obtaining a macromolecule-solid support complex, b. converting the solvent system for said complex to a predominantly organic solvent system c. reacting said small molecular mass molecule and said solid support-macromolecule in a solvent, and d. washing said solid support-macromolecule-small molecular mass molecule complex by a solvent, wherein the solvent is predominantly organic in at least step c or step d.

* * * * *